United States Patent [19]

DeSatnick et al.

[11] Patent Number: 4,650,462
[45] Date of Patent: Mar. 17, 1987

[54] IRRIGATION SYSTEM

[75] Inventors: Allen H. DeSatnick, Marblehead; Herbert D. Marcus, Winchester, both of Mass.

[73] Assignee: Minnesota Mining and Manufacturing Company, St. Paul, Minn.

[21] Appl. No.: 760,171

[22] Filed: Jul. 29, 1985

[51] Int. Cl.$^4$ .............................................. A61M 1/00
[52] U.S. Cl. ................................... 604/30; 128/24 A; 128/51; 128/67
[58] Field of Search ............... 604/30, 19, 65, 66, 604/67, 151, 153, 31–35, 22, 51; 128/24 A, 66

[56] References Cited

U.S. PATENT DOCUMENTS

| | | | |
|---|---|---|---|
| 3,930,505 | 1/1976 | Wallach | 604/22 |
| 4,117,843 | 10/1978 | Banko | 604/65 |
| 4,180,074 | 12/1979 | Murry et al. | 604/66 |
| 4,203,444 | 5/1980 | Bonnell et al. | 128/276 |
| 4,261,360 | 4/1981 | Perez | 128/230 |
| 4,395,258 | 7/1983 | Wang et al. | 604/51 |

OTHER PUBLICATIONS

Arthro-Automat 5002, Technical Disclosure, Manufactured by F. M. Wiest KG.
O'Connor's Textbook of Arthroscopic Surgery, pp. 169–178, Acute Knee Arthroscopy.

Primary Examiner—C. Fred Rosenbaum
Assistant Examiner—Gene B. Kartchner
Attorney, Agent, or Firm—Donald M. Sell; James A. Smith; Robert W. Hoke, II

[57] ABSTRACT

An irrigation system for use in arthroscopic surgery including a variable RPM pump for introducing irrigation fluid from a fluid supply to a body irrigation site, a pressure control valve in the outflow from the irrigation site, a pressure sensor and associated controller for sensing pressure at the site and adjusting the pressure control valve for maintenance of the pressure within predetermined parameters, an override controller responsive to an inability to maintain pressure within the set parameters and responsive thereto to vary the flow rate of the pump, and associated display and signal components. The flow rate and pressure are individually and independently controllable.

11 Claims, 2 Drawing Figures

IRRIGATION SYSTEM

BACKGROUND OF THE INVENTION

The invention herein is broadly concerned with endoscopic procedures, and more particularly with arthroscopic surgery.

Arthroscopic surgery is a minimally invasive therapeutic and/or diagnostic procedure, during which small sized visualization and surgical tools are introduced into a joint cavity (most commonly a knee) through very small incisions. Typically, at least three incisions are employed for a therapeutic procedure and at least two for a diagnostic procedure. During the surgery, irrigation of the joint is necessary for the following reasons:

(1) Inflation of the joint is desirable for better visualization and access achieved by an increased joint or tissue separation. This is accomplished by application of pressure through the medium of the irrigation fluid.

(2) Flow of the irrigation fluid through the joint keeps the field of view clear and eliminates any loose debris.

(3) The fluid keeps the joint lubricated and replaces lost body fluids.

There are thus two independent factors at work here, the pressure and the flow rate of the irrigation fluid. The function and need for independent control of these two factors can be illustrated by the following situations:

(a) There are times during the surgical procedure when one needs to view and reach the far or posterior end of the joint. The joint separation needs to be increased without any need for an increased flow. A higher pressure in the joint will achieve this.

(b) If there is debris or bleeding in the cavity, a quick flush of fluid is needed to clear the field of view. Such conditions require a higher fluid flow rate without a higher pressure, assuming the joint separation is adequate.

(c) When an accessory instrument, like a shaver with wall suction, is used, a higher fluid inflow is required to keep up with the increased demand and prevent the joint from collapsing. A higher flow rate but the same set pressure is needed here.

Currently, the typical solution is to use saline bags hung above the patient's level. The bags are raised to obtain more pressure and the flow rate is controlled by using variable clamps on the tubing leading to and away from the patient. The control for the two operations is manual and decided upon by the surgeon.

An automated pressure regulating system, manufactured by F. M. Wiest KG of Germany, utilizes a pump with pressure measured in the joint and a feedback used to control the pump speed (flow rate). If the pressure is low, the pump automatically speeds up to compensate, and if the pressure is high, the pump slows down. In this system, the flow is dependent on the desired pressure and cannot be controlled independently.

U.S. Pat. No. 4,261,360, issued Apr. 14, 1981 to Jose A. Perez, discloses a two pump irrigation system for transurethral irrigation to maintain a constant volume of fluid in a bladder. If there is no bleeding, the inflow and outflow rates will be the same and the bladder, if not disturbed, will maintain a constant volume and hence constant pressure. It will also do so if there is bleeding into the bladder. However, if there is an increase in bladder pressure due to a compression of the bladder (no significant change in volume), the Perez system will neither detect it nor take any corrective action. Also, if there is any leakage from the bladder, the Perez system will not compensate for that loss. This could result in a decreased bladder fluid volume (distension) and pressure. To obtain a higher distension/pressure in the system, a higher flow rate would need to be selected manually.

SUMMARY OF THE INVENTION

The proposed irrigation system is unique in that it allows independent control of both pressure and flow. The system can be set to operate at any preselected values of pressure and flow rate. Once these are selected, the system automatically operates to maintain these values. If, however, there is a conflict between achieving these two values (due to leakage, etc.), it is the pressure value that will be maintained at the expense of the flow rate. This is because, of the two, pressure is the more critical factor. An increased pressure can cause damage to the body. It can lead to fluid extravasation (seepage) into the surrounding soft tissues and if high enough, can rupture the capsule. High pressures can be caused by increased fluid inflow and very high pressures can also occur when a joint is flexed. Thus, continuous monitoring and control of pressure in the cavity are necessary and important.

In the system, the source of irrigating fluid may be standard saline bags with the fluid fed to the pump through tubing of approximately 3/16" inner diameter. The discharge of the pump then feeds to the knee or other irrigation site through the same type of tubing. The fluid is introduced into the knee through an appropriate cannula. The sensing of pressure at the site will normally be effected by pressure sensing tubing directly communicated with the site through a dedicated cannula. The pressure sensing may also be done either through a port in the fluid introducing cannula or in the outflow line.

Exit from the knee or body irrigation site will normally be made through a standard cannula with the outflow tubing or line running therefrom to an appropriate suction source. If desired, the outflow tubing may merely run to a collection bucket, normally placed at floor level below the height of the irrigation site.

A pressure controlled valve is provided in the outflow line and is operable in response to the sensed pressure at the site. The valve may be either a proportional or solenoid valve. If a solenoid valve is used, it is also contemplated that an expansion chamber be provided upstream thereof for dampening the pulsing of the "on/off" operation thereof.

The pressure sensing tubing, preferably 1/16" I.D., extends from the site, or immediately adjacent thereto, to a sensing element incorporated in the pump cabinet. This portion of the system is sealed, and the pressure tubing run dry with no liquid flow going therethrough. The preferred transmission medium for the pressure from the site to the sensor is air. A small microbial filter will be incorporated in the pressure line to maintain sterility and eliminate the necessity of sterilizing the sensor in the pump after each procedure.

While other configurations are possible, it is contemplated that the pump incorporate two settings for pressure and three settings for flow, all of which may be independently preset. Appropriate push-button switches allow for a quick selection of low or high pressure and low, medium or high flow. It is also contemplated that, for purposes of convenience, an appropriate foot switch be provided for setting selection at the convenience of the surgeon.

With regard to pressure maintenance, the output of the pressure sensor or transducer is fed to a pressure controller, the parameters of which have been set by switch and which, in turn, controls the pressure control valve in the outflow line for a maintenance of the pressure. The flow rate or volume will be maintained as set by switch through constant pump RPM. Any change in the manual pressure setting will be automatically maintained by the pressure sensing and control system through valve manipulation and independent of the constantly maintained volume or flow. Similarly, any manual resetting of the pump RPM to change the volume or flow rate will have no affect on the preset pressure parameters which are maintained through the pressure sensing and control system and the pressure control valve operative thereby as the actual pressure stabilizing means.

It is foreseeable that, under some circumstances, the system will be unable to continuously maintain the desired pressure level at the selected flow rate. For example, it is conceivable that the demands of the suction system associated with a shaver procedure will be such as to exceed the pressure accommodating capability at the selected flow rate. In such circumstances, the system of the invention provides for an override controller which, sensing the inability of the pressure controller to maintain the pressure parameters, will override the manual or switch setting of the pump RPM, and adjust the flow rate to a point at which the pressure can be maintained within the desired parameters. The override controller acts in a manner whereby the flow rate will automatically drop back to the original setting upon removal of the excessive demand. The system will preferably include a visual indication, for example a light, of a flow override situation. Other displays, as deemed desirable, will also be provided.

DESCRIPTION OF THE PREFERRED EMBODIMENT

Figure 1:
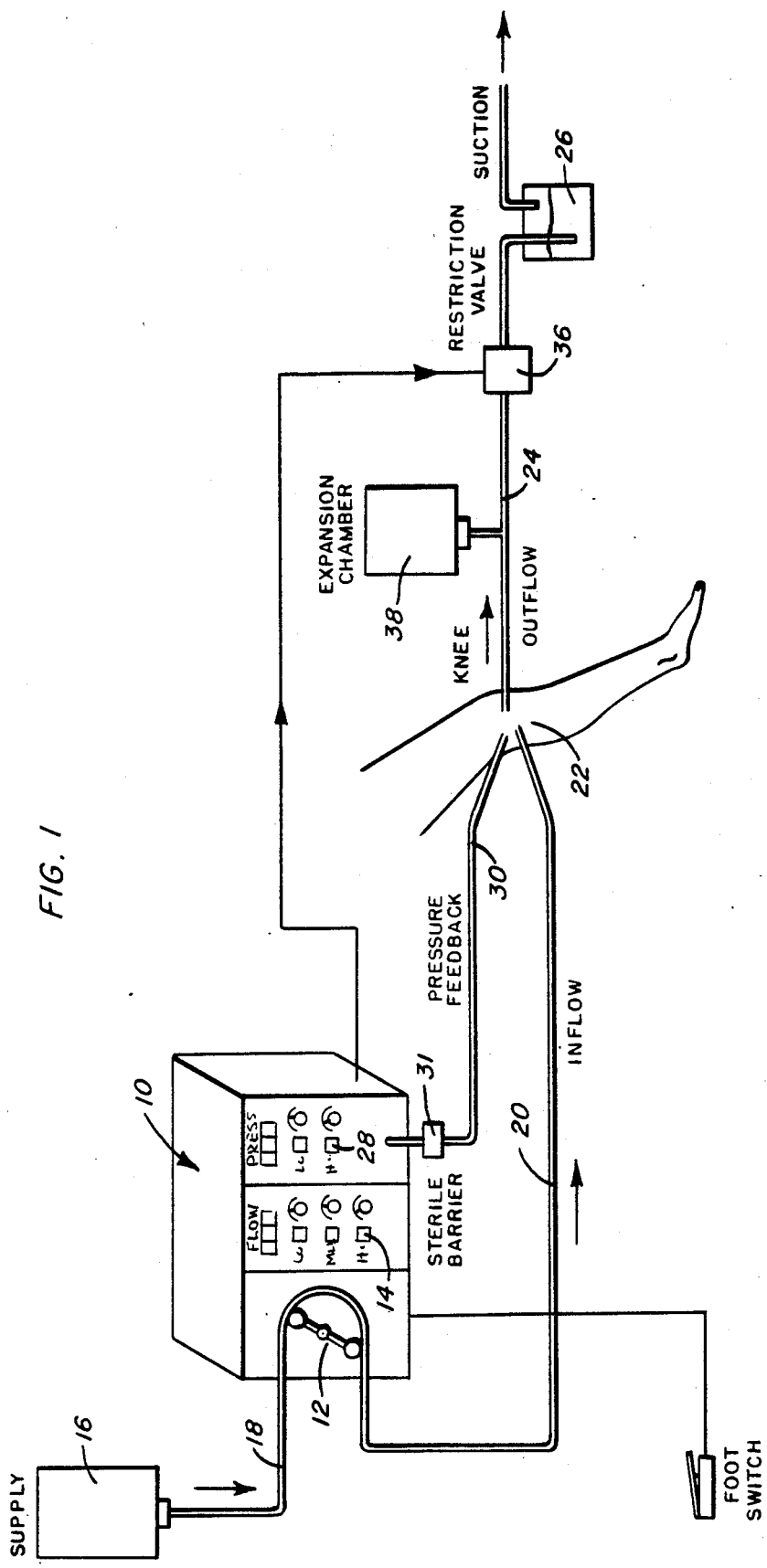
FIG. 1 is a schematic illustration of the system of the invention.
Figure 2:
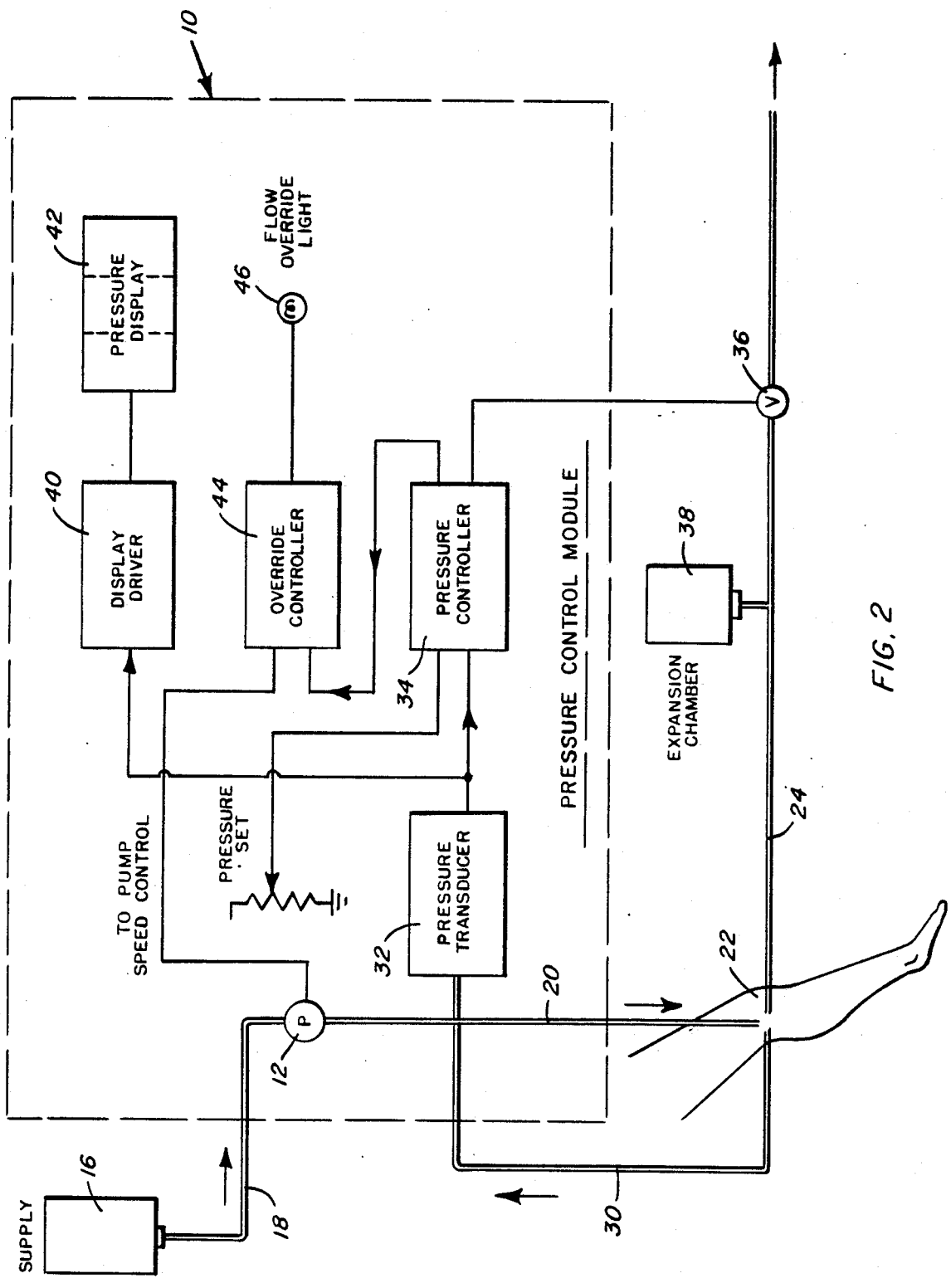
FIG. 2 is a schematic block diagram of the invention.

Referring now more specifically to the drawings, it is contemplated that the control components of the system be incorporated in an enlarged pump housing or cabinet 10, providing an environment with minimal external components. The pump 12 will preferably be a peristaltic pump with three manual RPM settings 14 for selectively providing constant low, medium or high flow.

The system includes or is supplied with fluid from an appropriate fluid source 16 which, as an example, may be the conventionally utilized series of irrigation fluid bags. The fluid is supplied to the pump through a supply conduit or tubing 18. An appropriate shutoff valve may, as desired, be incorporated in this line immediately downstream of the fluid supply 16. The fluid is normally gravity fed to the pump 12 and in turn discharged from the pump 12 through a second conduit, the inflow line or tube 20, at a constant flow rate determined by the preset RPM of the pump.

The inflow line 20 communicates with the irrigation body site 22, a knee in the illustrated embodiment, through an appropriate cannula. Exit of the flow from the knee is similarly effected through an appropriate cannula and outflow line or tube 24. This outflow line 24 will communicate, at the discharge, with appropriate discharge apparatus 26 which may consist of a lower level collection bucket or an appropriate suction system.

The desired pressure at the irrigation site 22, similar to the flow rate, will also be manually set through an appropriate series of switches 28 with the pressure continuously monitored and automatically adjusted, as required, to stay within set predetermined parameters. The actual sensing of pressure utilizes a pressure sensing or pressure feedback tube 30 communicating, at one end, with the knee site 22 or, alternatively, the inflow or outflow tubes 22 and 24 immediately outward of the site 22. This pressure feedback tube 30, on the order of 1/16" I.D., will utilize air as the pressure transmission medium, and as such will be maintained dry. An appropriate sterile barrier 31, in the nature of a small microbial filter, will be incorporated in the feedback line to maintain sterility and thus eliminate the necessity of sterilizing the components inward thereof, and in particular the sensor or pressure transducer 32 with which the feedback line directly communicates.

The output of the sensor or pressure transducer is fed to a pressure controller 34 which detects variations in the pressure from the selected parameters and provides for a controlled adjustment in a restriction or pressure control valve 36 provided in the outflow line 24. This valve 36 will preferably be a solenoid operated valve with the anticipated pulsing of the "on/off" valve being dampened out of the system by an appropriate expansion chamber or accumulator 38 in or in communication with the outflow line 24 upstream of the valve 36. As an example, it is calculated that an expansion chamber of approximately one liter will filter or dampen the pressure variation to less than 1%, with a valve repetition rate of approximately one cycle per second in the environment of the invention. As an alternative to a solenoid operated valve, an appropriate linear or proportional valve can be used, thus reducing or eliminating the necessity for the expansion chamber.

It is to be appreciated that the pressure adjustment, for maintenance thereof within the preselected parameters, is effected without recourse to the preselected flow, requiring, under normal circumstances, no variation in the flow rate or the fluid volume at the site resulting therefrom. Should a greater flow rate be desired, for a flushing of debris from the site or the like, the appropriate switch can be manually activated and the pump RPM changed. The pressure controller 34 will automatically accommodate itself to the change in flow rate and continue to maintain the pressure within the preset parameters through a continuous monitoring of the pressure by the transducer and a control signaling of the valve 36. As desired, appropriate RPM and pressure displays 40 and 42 may be provided on the housing 10.

In some circumstances, a surgeon, or the procedure involved, will require a pressure that cannot be maintained at the flow rate set for the pump 12. This may be due to leakage from other incisions, the demands of a separate suction system associated with the particular tool being used, and the like. In such case, the feedback from the pressure control module or pressure controller 34 indicating, as an example, a low pressure, i.e. 10% below the selected pressure, existing for a period of time greater than allowed, i.e. four seconds, will be sensed by an override controller 44. The override controller 44, in turn, will automatically override the manual setting of the pump RPM to increase the flow rate of the pump to a higher setting whereat the automatic operation of the pressure controller should be able to attain the desired pressure. Upon attaining said pressure, the override controller 44 will return the pump RPM to the original manual setting.

It is also possible, while considered unlikely, that the suction discharge system and pressure controller may not be able to keep up with the desired flow rate of the pump, for example due to failure of the vacuum or blockage of the suction tubing. In such case, the sensed sustained pressure will, through the pressure controller and override controller, reduce the flow rate of the pump, and thus facilitate maintenance of the desired pressure through automatic control of the pressure control valve 36. Such unusual condition, whether generated by excessive high or low pressure, will be visually indicated by the flow override light 46. Further, when the particular procedure, or other cause for an overriding of the set flow rate, is no longer involved or present, the override controller provides for an automatic return to the original RPM setting for the pump.

The system of the present invention also incorporates various safety factors whereby, upon a sensing of extreme pressure variations, for example an uncontrollable pressure increase of 20% higher than the selected value, appropriate means are activated to shut down the system, immediately stopping the pump, opening the pressure control valve, and draining fluid until pressure returns to the selected value. An emergency light will be provided to signal this situation. As desired, the pump may restart once the pressure has dropped to a safe value.

While not restricted thereto, it is contemplated that the pump system be designed to operate in the following ranges:
 1. Flow rates 0–999 ml/min.
 2. Pressure 0–100 mm Hg.

The operative components, controllers, and the like, of the system are, in and of themselves, of known construction and performance capability. Broadly, pressure is sensed by means of a needle or cannula inserted into the knee. The cannula mounts a small diameter plastic tube going to the pump. The pressure is transmitted through this plastic tube by means of air and is sensed by a standard solid-state pressure sensor which may consist of laser trimmed resistors on a silicon die. The differential voltage produced by the pressure is isolated and then amplified to produce an actual pressure voltage which is fed into an input of a comparator. The other input of the comparator has on it the steady voltage representing the selected pressure level. If the actual pressure is less than the desired pressure, the output of the comparator will be positive. The resulting positive voltage will switch on a transistor and thus produce current in the solenoid valve and close the solenoid. This closing of the solenoid will block the outflow line from the knee, and will result in an increase of pressure, since the pump will be running, fluid will be coming in, and the outflow is blocked. When the actual pressure becomes greater than the desired pressure, the reverse condition will occur, and the comparator will have a zero output. This zero output will result in switching off the transistor and will cut off the current in the solenoid. The solenoid will therefore open, and fluid will drain out of the knee, resulting in a reduction of pressure. It can therefore be seen that the actual pressure will be held quite closely around the desired pressure point. As soon as pressure increases, the solenoid will open and drain some fluid out of the knee. When pressure falls, the solenoid will close and pressure in the knee will build back to the desired value.

The tendency for excessive operation of the solenoid is precluded by the expansion chamber in the outflow line ahead of the solenoid that acts as a pressure reservoir or pressure stabilizing device. The particular solenoid valve used is not critical to the operation, but one which may be used for the system is manufactured by Angar Scientific, a subsidiary of Asco, part #P/N:388N0121215. It is rated 15 pounds per square inch, 12 volts DC. The pressure transducer contemplated is supplied by Omega Engineering Inc. of Stamford, Conn., part #PX136.

The override logic basically involves a feeding of the selected pressure voltage and the actual pressure voltage to a further comparator, the output from which is determined by a combination of a differential in the pressure voltages and a time factor.

The system of the invention does what none of the currently available systems do—it permits independent control of the pressure and flow rate values and it automatically adjusts the outflow and, if necessary, the pump speed to maintain the selected pressure. Similarly, if a larger joint separation is needed, the system may be manually set at a higher demand pressure. Once this is set, it will automatically maintain the new set values. During a typical procedure, the desired pressure may be changed once or twice. For the most part, one value is used and the outflow rate automatically varies to meet the demands of the surgical procedure. This makes for safe operating conditions with the danger of over-pressurization being minimal, thus permitting the surgeon to concentrate on the procedure rather than be concerned about flow or pressure in the joint. This invention is likely to reduce the operating room time for the procedure.

It should be noted that the irrigating fluid flows through closed, flexible tubings at all times, including when passing through the valve and pump head. The sterility of the fluid is not compromised at any time.

Built-in safety features in the system automatically shut it down if a predetermined high pressure level is reached. Also, both audio and visual alarms to alert the surgeon of a high pressure situation can be provided. If, for any reason, the system does not shut down, a mechanical relief valve may be included to relieve the high pressure. Further, an electronic safety circuit is to be included to detect the absence of pressure sensing and shut off the pump if it is determined that the pressure sensing has been compromised.

The system will operate as follows. First, the surgeon will select the desired flow rate and the desired pressure for distension. The flow rate will determine the speed, and thus the flow, of the pump. When pressure in the knee starts to exceed the selected pressure, the control valve in the suction or outflow line opens and allows the pressure to drop. Conversely, as long as the pressure is below that selected, the valve will remain closed. Thus, the pressure of the fluid solution in the knee will be held to very close tolerance.

If the surgeon requires more or less volume from the system, the flow rate of the pump can be adjusted and the pressure module will automatically compensate for the change by controlling the valve in the suction line.

For example, if more flow is desired, it is only necessary to increase the flow setting, and thus the RPM of the pump. The system will respond as necessary by either opening the output solenoid for longer periods of time or more often, so that the increase in flow is not accompanied by an increase in pressure. Thus, the pressure will be unchanged with the new volume setting. Similarly, if more or less pressure were desired, the surgeon would change the setting of the pressure module, and again the operation would be automatic with the system adapting to the new setting with no change in volume.

There may be times when a surgeon will desire a pressure that cannot be maintained at the selected flow rate, due to leakage from incisions, or the use of a separate instrument using suction. In this case, feedback from the pressure module will automatically increase the flow rate of the pump to the required volume to maintain the desired pressure. This "override" condition would be automatic and would activate the flow override indicator on the unit. It is also possible; though unlikely, that the suction system and pressure controller cannot keep up with the desired flow rate of the pump, for example due to failure of the vacuum, or blockage of the suction tubing. In this case, the feedback from the pressure module to the pump will reduce the flow rate of the pump, again activating the flow override indicator, and maintaining the desired pressure.

This system will normally have the capability of setting and displaying desired flow rates from the front panel. The three settings will be constantly displayed, with the one selected being brighter than the other two. Selection of the desired rates will be accomplished by the selection buttons on the front of the panel or by a foot switch at the surgeon's control. The distension pressure can also be varied either by means of the selection buttons on the front panel or by a foot switch.

We claim:

1. An irrigation system for use in endoscopic procedures for maintaining and controlling pressure and flow of irrigation fluid to an internal body irrigation site, said system comprising:
    (a) fluid source means for providing a supply of irrigating fluid;
    (b) pump means for pumping irrigation fluid, said pump means including a pump, adjustable pump drive means for driving said pump at preselected flow rates, first conduit means communicating said fluid source means with said pump, and second conduit means communicating said pump to an irrigation site to deliver the full flow of irrigating fluid thereto at said preselected flow rate;
    (c) outflow conduit means in fluid receiving communication with said irrigation site and defining a fluid flow discharge for said irrigation fluid;
    (d) adjustable flow controlling valve means for selectively varying fluid flow discharge through said outflow conduit means for regulation of positive fluid pressure at said irrigation site;
    (e) pressure sensing means for measuring pressure at said irrigation site and sensing of pressure variations directly within said site;
    (f) pressure control means, responsive to said pressure sensing means, for selectively adjusting said adjustable flow controlling valve means for maintaining pressure at said irrigation site within predetermined parameters independently of said pump drive means and the flow rate developed thereby; and
    (g) manual means for adjusting the pump drive means, and thereby selecting a flow rate, independently of said pressure sensing means and said predetermined parameters.

2. The system of claim 1 including override control means for sensing inability of said pressure control means to maintain pressure within said predetermined parameters and, in response thereto, adjusting said pump drive means, independently of said manual means, to override said manual means and selectively adjust said flow rate.

3. The system of claim 2 including manual means for adjusting said predetermined pressure parameters.

4. The system of claim 3 wherein said adjustable flow controlling valve means comprises a solenoid operated valve.

5. The system of claim 4 including expansion chamber means communicating with said outflow conduit means upstream of said adjustable flow controlling valve means.

6. The system of claim 3 wherein said pressure sensing means comprises pressure feedback conduit means communicating directly between said irrigation site and said pressure control means.

7. The system of claim 6 wherein said pressure sensing means utilizes a dry pressure transmission medium within said pressure feedback conduit means, and a pressure sensing transducer.

8. The system of claim 3 wherein said pressure sensing means comprises a pressure feedback conduit means communicated with one of said second conduit means and said outflow conduit means.

9. The system of claim 3 including a visual flow override indicator responsive to said override control means.

10. The system of claim 3 wherein said adjustable flow controlling valve means comprises a proportional valve.

11. Method of delivering a supply of irrigation fluid to an internal body irrigation site and independently and selectively maintaining the flow and pressure parameters within predetermined limits comprising the steps of:
    (1) establishing ingress and egress communication conduits with the selected body site;
    (2) introducing irrigation fluid into and out from said site through said conduit, and establishing positive pressure Parameters within preselected limits within said site;
    (3) monitoring (measuring) the pressure of said irrigation fluid within said site and independently controlling said pressure by controlling the egress of said irrigation fluid out from said site and selectively adjusting said pressure and said flow independently of each other.

* * * * *